(12) United States Patent
Nagy

(10) Patent No.: US 6,596,826 B1
(45) Date of Patent: Jul. 22, 2003

(54) OLEFIN POLYMERIZATION CATALYSTS CONTAINING 1,3-DIBORETANYL LIGANDS

(75) Inventor: Sandor Nagy, Naperville, IL (US)

(73) Assignee: Equistar Chemicals, LP, Houston, TX (US)

( * ) Notice: Subject to any disclaimer, the term of this patent is extended or adjusted under 35 U.S.C. 154(b) by 26 days.

(21) Appl. No.: 10/027,130

(22) Filed: Dec. 20, 2001

(51) Int. Cl.$^7$ ................................................. C08F 4/44
(52) U.S. Cl. ........................ 526/134; 526/131; 526/133; 526/160; 526/161; 526/170; 526/172; 502/103
(58) Field of Search ................. 526/131–134, 526/160, 170, 161, 172

(56) References Cited

U.S. PATENT DOCUMENTS

| | | | |
|---|---|---|---|
| 4,752,597 A | 6/1988 | Turner | 502/104 |
| 4,791,180 A | 12/1988 | Turner | 526/160 |
| 5,064,802 A | 11/1991 | Stevens et al. | 502/155 |
| 5,153,157 A | 10/1992 | Hlatky et al. | 502/117 |
| 5,198,401 A | 3/1993 | Turner et al. | 502/155 |
| 5,241,025 A | 8/1993 | Hlatky et al. | 526/129 |
| 5,414,180 A | 5/1995 | Geerts et al. | 585/525 |
| 5,539,124 A | 7/1996 | Etherton et al. | 548/402 |
| 5,554,775 A | 9/1996 | Krishnamurti et al. | 556/7 |
| 5,637,659 A | 6/1997 | Krishnamurti et al. | 526/133 |
| 5,637,660 A | 6/1997 | Nagy et al. | 526/160 |
| 5,648,440 A | 7/1997 | Sugano et al. | 526/132 |
| 5,902,866 A | 5/1999 | Nagy et al. | 526/133 |
| 6,211,311 B1 | 4/2001 | Wang et al. | 526/131 |
| 6,228,959 B1 | 5/2001 | Nagy | 526/134 |
| 6,232,260 B1 | 5/2001 | Nagy et al. | 502/155 |

OTHER PUBLICATIONS

Willerhausen, P.; Kybart, C.; Stamatis, N.; Massa, W.; Bühl, M.; Schleyer, P. v. R.; Berndt, A. Angew. Chem., Int. Ed. Engl. 1992, 31, 1238–1240.*
Pilz, M.; Allwohn, J.; Willerhausen, P.; Massa, W.; Berndt, A. Angew. Chem., Int. Ed. Engl. 1990, 29, 1030–1032.*
Pilz, M.; Allwohn, J.; Bühl, M.; Schleyer, P. v. R.; Berndt, A. Z. Naturforsch. 1991, 46b, 1085–1090.*
Karger et al. Chem Ber. 1989, 122, 1881–1889.*
J. March, *Advanced Organic Chemistry*, 2d ed. (1977) pp. 55–59.
Chem. Ber. 122 (1989) 1881.
Angew. Chem., I.E. Engl. 25 (1986) 1112.
Siebert et al. Angew. Chem., I.E. Engl. 24 (1985) 759.
Chem. Ber. 126 (1993) 2003.
Paetzold et al. Chem. Ber. 126 (1993) 1565.
Chem. Ber. 122 (1989) 1057.
J. Organometal. Chem. 249 (1983) 23.
P. Hornbach et al. Angew. Chem., I.E. Engl. 25 (1986) 1112. (Angew. Chem. 98 (1986) 1121).
S. Grundel et al., Chem. Ber. 129 (1996) 1233.

* cited by examiner

Primary Examiner—David W. Wu
Assistant Examiner—Rip A Lee
(74) Attorney, Agent, or Firm—Jonathan L. Schuchardt

(57) ABSTRACT

An olefin polymerization catalyst system and method of making it are disclosed. The catalyst system comprises an activator and an organometallic complex. The complex comprises a Group 3 to 10 transition or lanthanide metal, M, and at least one anionic 1,3-diboretanyl ligand that is bonded to M. Molecular modeling results indicate that catalysts from organometallic complexes that incorporate anionic 1,3-diboretanyl ligands will rival the performance of traditional metallocenes.

14 Claims, No Drawings

OLEFIN POLYMERIZATION CATALYSTS CONTAINING 1,3-DIBORETANYL LIGANDS

FIELD OF THE INVENTION

The invention relates to catalysts useful for olefin polymerization. In particular, the invention relates to organometallic catalysts that incorporate at least one anionic 1,3-diboretanyl ligand.

BACKGROUND OF THE INVENTION

Interest in single-site (metallocene and non-metallocene) catalysts continues to grow rapidly in the polyolefin industry. These catalysts are more reactive than Ziegler-Natta catalysts, and they produce polymers with improved physical properties. The improved properties include narrow molecular weight distribution, reduced low molecular weight extractables, enhanced incorporation of α-olefin comonomers, lower polymer density, controlled content and distribution of long-chain branching, and modified melt rheology and relaxation characteristics.

Traditional metallocenes commonly include one or more cyclopentadienyl groups, but many other ligands have been used. Putting substituents on the cyclopentadienyl ring, for example, changes the geometry and electronic character of the active site. Thus, a catalyst structure can be fine-tuned to give polymers with desirable properties. Other known single-site catalysts replace cyclopentadienyl groups with one or more heteroatomic ring ligands such as boraaryl (see, e.g., U.S. Pat. No. 5,554,775) or azaborolinyl groups (U.S. Pat. No. 5,902,866).

Single-site catalysts typically feature at least one polymerization-stable, anionic ligand that is aromatic, as in a cyclopentadienyl system. All five carbons in the planar cyclopentadienyl ring participate in bonding to the metal in η-5 fashion. The cyclopentadienyl anion functions as a 6π-electron donor. Similar bonding apparently occurs with some heteroatomic ligands such as boratabenzenyl or azaborolinyl. Catalysts that incorporate bicyclic "homoaromatic" anions (also 6π-electron donors) have also been described (see U.S. Pat. No. 6,228,959).

The anionic ligands described to date are normally "conjugated" ring systems. Electron density in the anions is thought to be "delocalized," or shared among three or more atoms in the ring. Some atoms may be bypassed, as in the bishomoaromatic ligands. Most of the known 6π-electron-donor ligands have five-membered rings (as in cyclopentadienyl or azaborolinyl), six-membered rings (as in borabenzenyl), or even seven-membered rings (e.g., the bishomoaromatic systems of the '959 patent). Delocalization of the electron density is presumed to impart stability to the anionic ligand. In practice, the ligands are often easily generated by deprotonating suitable precursors (e.g., cyclopentadiene). The relatively high acidity of cyclopentadiene is a reflection of a high degree of stabilization of its conjugate anion.

Anion stability, however, is only one factor in making stable organometallic complexes. Consider cyclobutadiene, which is "anti-aromatic," unstable, and cannot be isolated at ordinary temperatures. In spite of its instability, cyclobutadiene can be "trapped" as a stable organometallic complex (see J. March, *Advanced Organic Chemistry*, 2d ed. (1977) pp. 55–59).

Thus, when evaluating the potential of organometallic complexes as catalysts for olefin polymerization, it is important to consider more than just the stabilities of the anionic ligands. It is also necessary to consider the degree to which the ligand helps to stabilize an incipient cationically active site. Moreover, the reactivity of the active site toward olefins and the rate of monomer insertion are also important. A ligand precursor with relatively low acidity might be valuable anyway if other factors (such as those noted above) are favorable. As is shown below, molecular modeling studies can help to identify valuable ligands and complexes.

Little is known about the prospect of using anionic ligands having four-membered rings to make organometallic complexes for olefin polymerizations. However, convenient synthetic routes to some interesting anionic, 1,3-diboretanyl ligands exist. Organometallic complexes from these ligands would provide a new class of potentially valuable catalysts to polyolefin producers

SUMMARY OF THE INVENTION

The invention is a catalyst system for polymerizing olefins. The catalyst system comprises an activator and an organometallic complex. The complex comprises a Group 3 to 10 transition or lanthanide metal, M, and at least one 1,3-diboretanyl anion that is bonded to M.

Evidence from molecular modeling studies suggests that catalysts incorporating anionic 1,3-diboretanyl ligands will rival the performance of catalysts based on cyclopentadienyl and substituted cyclopentadienyl ligands, i.e., traditional metallocenes.

The invention includes some straightforward synthetic routes to olefin polymerization catalysts that incorporate the 1,3-diboretanyl ligands. The ease and flexibility of these techniques put polyolefin makers in charge of a new family of catalysts.

DETAILED DESCRIPTION OF THE INVENTION

Catalyst systems of the invention comprise an activator and an organometallic complex. The catalysts are likely to be "single site" in nature, i.e., they are distinct chemical species rather than mixtures of different species. Single-site catalysts normally give polyolefins with characteristically narrow molecular weight distributions (Mw/Mn<3) and good, uniform comonomer incorporation.

The organometallic complex includes a Group 3 to 10 transition or lanthanide metal, M. More preferred complexes include a Group 4 to 6 transition metal; most preferably, the complex contains a Group 4 metal such as titanium or zirconium.

The organometallic complex also comprises at least one anionic 1,3-diboretanyl ligand that is bonded to the metal. By "1,3-diboretanyl," we mean a monoanionic ligand that has two boron atoms at opposite "corners" of a four-membered ring. The ligand further includes a carbanionic center, which resides between the two borons, and carbon or a heteroatom (oxygen, sulfur, phosphorus, or nitrogen) at the fourth corner. Thus, the anionic 1,3-diboretanyl ligand is either a 2-pi electron donor (with carbon at the fourth corner) or a 4-pi electron donor (with a heteroatom at the fourth corner).

Preferably, the anionic 1,3-diboretanyl ligand has the structure:

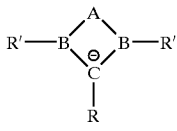

in which A is O, S, NR, PR, or CR$_2$; and each of R and R' is independently hydrogen, C$_1$–C$_{30}$ hydrocarbyl, dialkylamino, halide, or organosilyl. A few exemplary anionic 1,3-diboretanyl ligands:

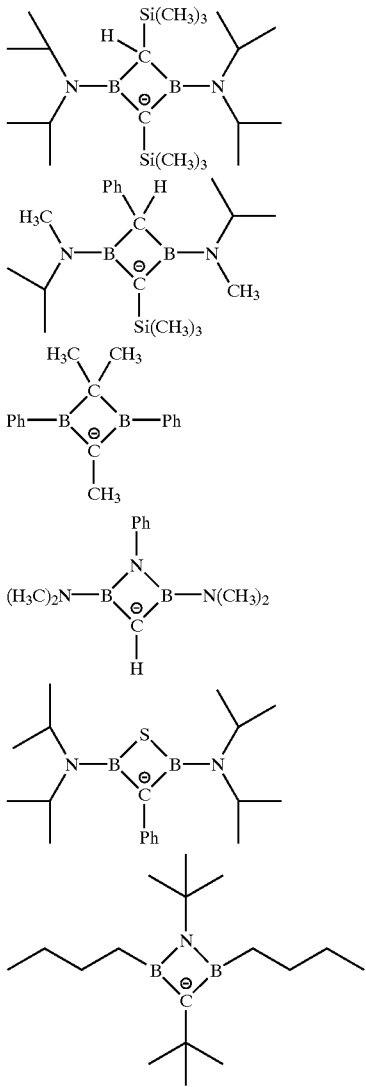

The anionic 1,3-diboretanyl ligands are conveniently generated by any suitable method. In one approach, they are made by deprotonating, using conventional means, suitable neutral precursors ("1,3-diboretanes") in which the 1,3-diboretane carbon is attached to at least one hydrogen atom. Normally, this hydrogen is the most acidic hydrogen in the precursor. As the calculations below demonstrate, the acidity of 1,3-diboretanes can exceed that of even cyclopentadiene, so deprotonation is facile. In another approach, described later, a synthetic equivalent of the 1,3-diboretanyl ligand is used to make the complex.

The 1,3-diboretanes preferably have the structure:

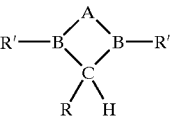

in which A is O, S, NR, PR, or CR$_2$; and each of R and R' is independently hydrogen, C$_1$–C$_{30}$ hydrocarbyl, dialkylamino, halide, or organosilyl.

The 1,3-diboretanes are made by any suitable method. One useful approach was developed by Siebert and coworkers (see *Chem. Ber.* 122 (1989) 1881 and *Angew. Chem., I.E. Engl.* 25 (1986) 1112). First, bis(trimethylsilyl)acetylene and tetrachlorodiborane react to give 1,1-bis(dichloroboryl)-2,2-bis(trimethylsilyl)ethylene (I). Reaction of (I) with 4 moles of diisopropylamine (with elimination of two moles of amine hydrochloride salt) replaces two chlorine atoms with diisopropylamino groups. Elimination of KCl by addition of two equivalents of potassium metal gives an unsaturated "diborete," which is easily hydrogenated using palladium on carbon at room temperature to produce 1,2-bis(diisopropylamino)-2,4-bis(trimethylsilyl)-1,3-diboretane (II):

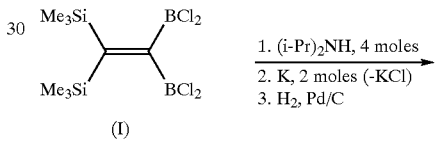

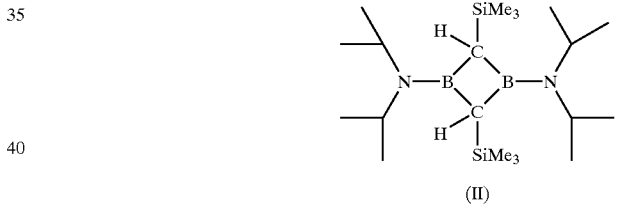

In another interesting approach developed by Siebert et al. (*Angew. Chem., I.E. Engl.* 24 (1985) 759), 1,2-bis(dichloroboryl)ethylene reacts with diisopropylamine to give an acyclic dichloride (III). Dehalogenation and ring closure with Na/K alloy gives a 1,2-dihydro-1,2-diborete (IV), which rearranges upon heating to 120° C. Subsequent hydrogenation gives a 1,3-diboretane (V):

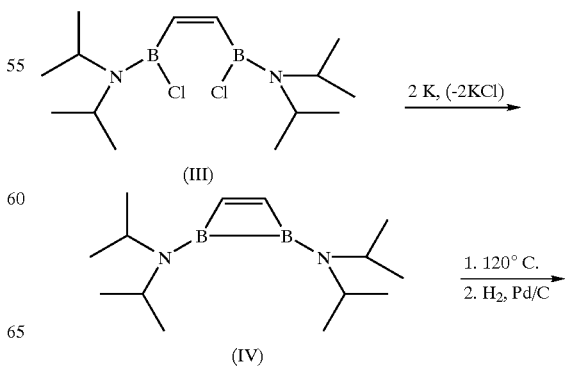

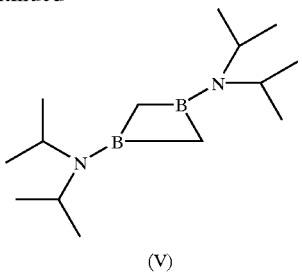

(V)

2-Aza-1,3-diboretanes are also suitable for use. They can be prepared, for example, by reacting a bis(haloboryl)methane or a bis(alkoxyboryl)methane (see *Chem. Ber.* 126 (1993) 2003) with a primary amine such as tert-butylamine with elimination of two moles of an alcohol or a protic acid (HCl, HBr, etc.):

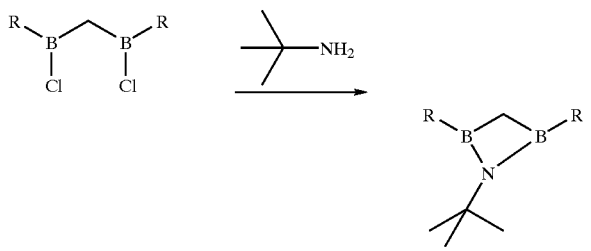

In another suitable approach, the method of Paetzold et al. (*Chem. Ber.* 126 (1993) 1565) is used to produce the 2-aza-1,3-diboretane. In one example of this method, two moles of an alkyl(t-butylimino)borane (VI) react with one mole of an alkylidene tantalum complex. The resulting cyclotrimerized tantalum complex, upon gentle warming, eliminates t-butyliminotantalum trichloride to give an azadiborocyclobutene, and conventional hydrogenation gives the desired 2-aza-1,3-diboretane (VII):

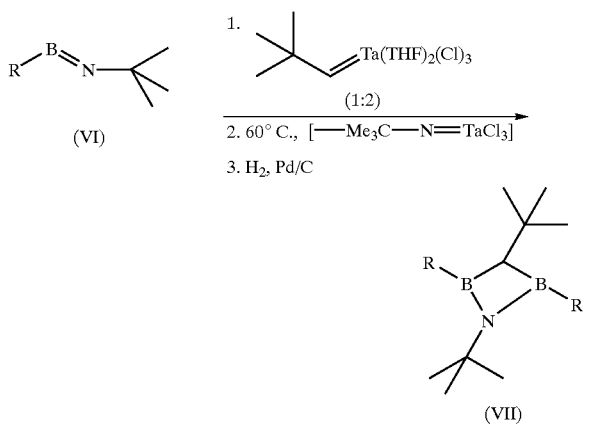

The organometallic complex optionally includes one or more additional polymerization-stable, anionic ligands. Examples include substituted and unsubstituted cyclopentadienyl, fluorenyl, and indenyl, or the like, such as those described in U.S. Pat. Nos. 4,791,180 and 4,752,597, the teachings of which are incorporated herein by reference. Other suitable polymerization-stable ligands are heteroatomic ligands such as boraaryl, pyrrolyl, indolyl, indenoindolyl, quinolinoxy, pyridinoxy, and azaborolinyl as described in U.S. Pat. Nos. 5,554,775, 5,539,124, 5,637,660, 5,902,866, and 6,232,260, the teachings of which are incorporated herein by reference. The organometallic complex also usually includes one or more labile ligands such as halides, alkyls, alkaryls, aryls, dialkylaminos, or the like. Particularly preferred are halides, alkyls, and alkaryls (e.g., chloride, methyl, benzyl).

The 1,3-diboretanyl anions and/or polymerization-stable ligands can be bridged. For instance, a —CH$_2$—, —CH$_2$CH$_2$—, or (CH$_3$)$_2$Si bridge can be used to link two 1,3-diboretanyl anions or a 1,3-diboretanyl anion and a polymerization-stable ligand:

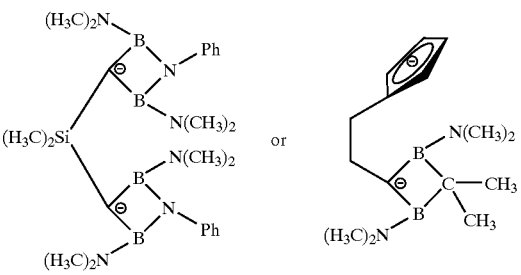

Groups that can be used to bridge the ligands include, for example, methylene, ethylene, 1,2-phenylene, and dialkyl silyls. Normally, only a single bridge is included. Bridging changes the geometry around the transition or lanthanide metal and can improve catalyst activity and other properties such as comonomer incorporation.

Preferred organometallic complexes have the structure:

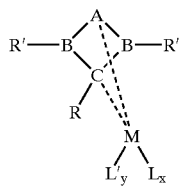

wherein M is a Group 3 to 10 transition or lanthanide metal. A is O, S, NR, PR, or CR$_2$; and each of R and R' is independently hydrogen, C$_1$–C$_{30}$ hydrocarbyl, dialkylamino, halide, or organosilyl. Each L is independently halide, alkoxy, siloxy, alkylamino, or C$_1$–C$_{30}$ hydrocarbyl. L' is substituted or unsubstituted cyclopentadienyl, indenyl, fluorenyl, boraaryl, pyrrolyl, indolyl, indenoindolyl, quinolinoxy, pyridinoxy, or azaborolinyl, y is 0 or 1, and x+y satisfies the valence of M.

"Constrained-geometry" complexes (see, e.g., U.S. Pat. No. 5,064,802) incorporating an anionic 1,3-diboretanyl ligand are also contemplated. For example:

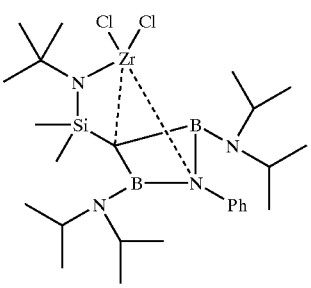

The catalyst system includes an activator. Suitable activators help to ionize the organometallic complex and activate the catalyst. Suitable activators are well known in the art. Examples include alumoxanes (methyl alumoxane (MAO), PMAO, ethyl alumoxane, diisobutyl alumoxane), alkylaluminum compounds (triethylaluminum, diethyl aluminum chloride, trimethylaluminum, triisobutyl aluminum), and the like. Suitable activators include acid salts that contain non-nucleophilic anions. These compounds generally consist of bulky ligands attached to boron or aluminum. Examples include lithium tetrakis(pentafluorophenyl) borate, lithium tetrakis(pentafluorophenyl)aluminate, anilinium tetrakis(penta-fluorophenyl)borate, and the like. Suitable activators also include organoboranes, which include boron and one or more alkyl, aryl, or aralkyl groups. Suitable activators include substituted and unsubstituted trialkyl and triarylboranes such as tris(pentafluorophenyl) borane, triphenylborane, tri-n-octylborane, and the like. These and other suitable boron-containing activators are described in U.S. Pat. Nos. 5,153,157, 5,198,401, and 5,241,025, the teachings of which are incorporated herein by reference. Suitable activators also include aluminoboronates—reaction products of alkyl aluminum compounds and organoboronic acids—as described in U.S. Pat. Nos. 5,414,180 and 5,648,440, the teachings of which are incorporated herein by reference.

The optimum amount of activator needed relative to the amount of organometallic complex depends on many factors, including the nature of the complex and activator, whether a supported catalyst is used, the desired reaction rate, the kind of polyolefin product, the reaction conditions, and other factors. Generally, however, when the activator is an alumoxane or an alkyl aluminum compound, the amount used will be within the range of about 0.01 to about 5000 moles, preferably from about 10 to about 500 moles, of aluminum per mole of transition metal, M. When the activator is an organoborane or an ionic borate or aluminate, the amount used will be within the range of about 0.01 to about 5000 moles, preferably from about 0.1 to about 500 moles, of activator per mole of M.

The activator is normally added to the reaction mixture at the start of the polymerization. However, when a supported catalyst system is used, the activator can be deposited onto the support along with the organometallic complex.

The catalyst systems are optionally used with an inorganic solid or organic polymer support. Suitable supports include silica, alumina, silica-aluminas, magnesia, titania, clays, zeolites, or the like. The support is preferably treated thermally, chemically, or both prior to use to reduce the concentration of surface hydroxyl groups. Thermal treatment consists of heating (or "calcining") the support in a dry atmosphere at elevated temperature, preferably greater than about 100° C., and more preferably from about 150 to about 600° C., prior to use. A variety of different chemical treatments can be used, including reaction with organo-aluminum, -magnesium, -silicon, or -boron compounds. See, for example, the techniques described in U.S. Pat. No. 6,211,311, the teachings of which are incorporated herein by reference.

The complex and activator can be deposited on the support in any desired manner. For instance, the components can be dissolved in a solvent, combined with a support, and stripped. Alternatively, an incipient-wetness technique can be used. Moreover, the support can simply be introduced into the reactor separately from the complex and activator.

The loading of complex on the support varies depending upon a number of factors, including the identities of the complex and the support, the type of olefin polymerization process used, the reaction conditions, and other concerns. Usually, the amount of complex used is within the range of about 0.01 to about 10 wt. % of transition metal based on the amount of supported catalyst. A more preferred range is from about 0.1 to about 4 wt. %.

The invention includes methods for making the organometallic complex. One method, illustrated by Example 4 below, involves deprotonating a 1,3-diboretane with at least one equivalent of a potent base such as lithium diisopropylamide, n-butyllithium, sodium hydride, a Grignard reagent, or the like. The resulting 1,3-diboretanyl anion is reacted with a Group 3 to 10 transition or lanthanide metal source to produce an organometallic complex. The complex comprises the metal, M, and at least anionic 1,3-diboretanyl ligand that is bonded to the metal.

Any convenient source of the Group 3 to 10 transition or lanthanide metal can be used. Usually, the source is a complex that contains one or more labile ligands that are easily displaced by the 1,3-diboretanyl anion. Examples are halides (e.g., $TiCl_4$, $ZrCl_4$), alkoxides, amides, and the like. The metal source can incorporate one or more of the polymerization-stable anionic ligands described earlier. The organometallic complex can be used "as is." Often, however, the complex is converted to an alkyl derivative by treating it with an alkylating agent such as methyl lithium. The alkylated complexes are more suitable for use with certain activators (e.g., ionic borates).

The 1,3-diboretanyl anion is preferably generated at low temperature (0° C. to −100° C.), preferably in an inert solvent (e.g., a hydrocarbon). The anion is then usually added to a solution of the transition or lanthanide metal source at low to room temperature. After the reaction is complete, by-products and solvents are removed to give the desired transition metal complex.

In another approach to making the complex, illustrated by Example 2 below, a synthetic equivalent of a 1,3-diboretanyl anion reacts with the Group 3–10 transition or lanthanide metal source. By "synthetic equivalent," we mean a neutral compound capable of generating an anionic 1,3-diboretanyl ligand under the reaction conditions. Suitable synthetic equivalents include 1,3-diboretanes that are C-substituted with —$QR''_3$ groups, where Q is Si, Sn, or Ge, and each R" is a $C_1$–$C_{30}$ hydrocarbyl group. When combined with suitable transition metal sources, particularly ones that have a labile anionic group such as halide or dialkylamino, a complex incorporating a 1,3-diboretanyl anion is produced with elimination of a neutral Sn, Ge, or Si-containing by-product. Usually, it suffices to combine the synthetic equivalent and the transition metal source in a suitable solvent and heat if needed to complete the reaction. For example:

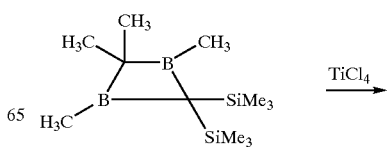

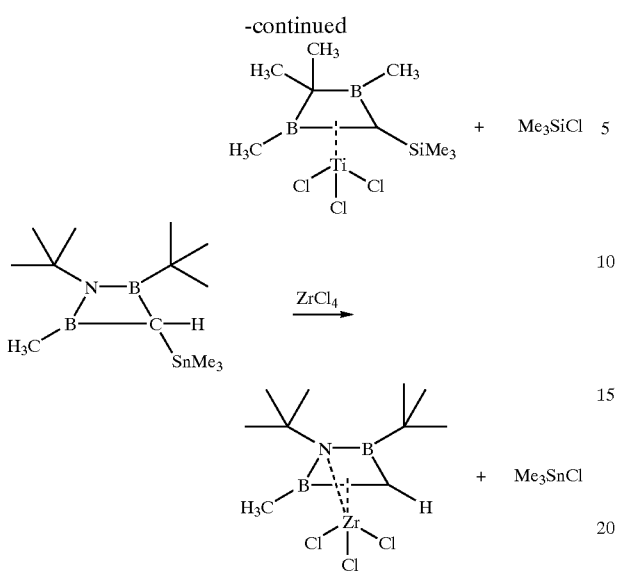

For more examples of suitable synthetic equivalents, see *Chem. Ber.* 122 (1989) 1057 and *J. Organometal. Chem.* 249 (1983) 23.

The catalysts are particularly valuable for polymerizing olefins. Preferred olefins are ethylene and $C_3$–$C_{20}$ α-olefins such as propylene, 1-butene, 1-hexene, 1-octene, and the like. Mixtures of olefins can be used. Ethylene and mixtures of ethylene with $C_3$–$C_{10}$ α-olefins are especially preferred.

Many types of olefin polymerization processes can be used. Preferably, the process is practiced in the liquid phase, which can include slurry, solution, suspension, or bulk processes, or a combination of these. High-pressure fluid phase or gas phase techniques can also be used. The process of the invention is particularly valuable for solution and slurry processes. Suitable methods for polymerizing olefins using the catalysts of the invention are described, for example, in U.S. Pat. Nos. 5,902,866, 5,637,659, and 5,539,124, the teachings of which are incorporated herein by reference.

The olefin polymerizations can be performed over a wide temperature range, such as about −30° C. to about 280° C. A more preferred range is from about 30° C. to about 180° C.; most preferred is the range from about 60° C. to about 100° C. Olefin partial pressures normally range from about 15 psia to about 50,000 psia. More preferred is the range from about 15 psia to about 1000 psia.

Catalyst concentrations used for the olefin polymerization depend on many factors. Preferably, however, the concentration ranges from about 0.01 micromoles per liter to about 100 micromoles per liter. Polymerization times depend on the type of process, the catalyst concentration, and other factors. Generally, polymerizations are complete within several seconds to several hours.

The following examples merely illustrate the invention. Those skilled in the art will recognize many variations that are within the spirit of the invention and scope of the claims.

EXAMPLE 1

Preparation of a 1,3-Diboretane Ligand

A 1,3-diboretane of structure (VIII)

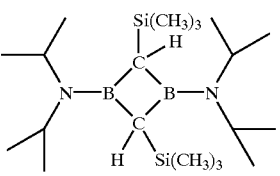

is prepared by the method of Siebert et al. (*Angew. Chem.* 98 (1986) 1121) by first reacting $B_2Cl_4$ with $Me_3SiCCSiMe_3$, followed by treatment with diisopropylamine to give $(Me_3Si)_2C=C[BClN(i-Pr)_2]_2$. Treatment of this product with $NaK_8$ and subsequent hydrogenation of the resulting diborate as described in the article gives the 1,3-diboretane (VIII).

EXAMPLE 2

Preparation of an Organometallic Complex

A toluene solution of the 1,3-diboretane from Example 1 (394 mg, 1.0 mmol of diboretane in 20 mL of toluene) is combined with an equimolar amount of cyclopentadienyltitanium trichloride (219 mg, 1.0 mmol in 20 mL of toluene) at −78° C. After warming to room temperature, the mixture is refluxed for 24 h, followed by removal of volatiles at reduced pressure. The residue, which contains an organometallic complex having the likely structure indicated below, is useful as a catalyst component for polymerizing olefins.

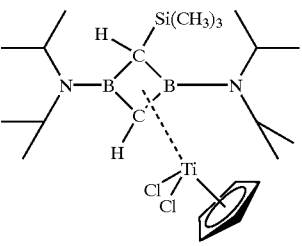

EXAMPLE 3

Ethylene Polymerization

A one-liter, stainless-steel reactor is charged with toluene (500 mL) and polymethalumoxane (2.2 mL of 4.14 M solution of PMAO in toluene, Al/Ti=2000). The reactor is charged with ethylene to 350 psig, and the contents are heated to 70° C. A toluene solution containing 2.5 mg of the 1,3-diboretanyl titanium complex is injected into the reactor to start the polymerization. Ethylene is supplied on demand to keep the reactor pressure constant at 350 psig. After about 1 hour, the reactor is vented to recover polyethylene as the expected product.

EXAMPLE 4

Preparation of an Organometallic Complex

To the 1,3-diboretane of Example 1 (394 mg, 1.0 mmol) in ether, tert-butyllithium (1.0 mL of 1.0 M solution in pentane) is added at −78° C. The reaction mixture is stirred at room temperature for 20 h. Cyclopentadienylzirconium trichloride (263 mg, 1.0 mmol) is added to the anion solution at −78° C., and the mixture is stirred at room temperature for 16 h. The resulting complex, which has the likely structure below, is used without further purification after removal of volatiles at reduced pressure.

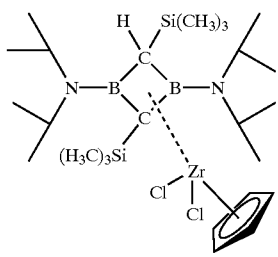

MOLECULAR MODELING STUDY

Additional evidence for the suitability of 1,3-diboretanyl anions as ligands for single-site catalysts comes from molecular modeling studies. All calculations have been performed with complete geometry optimization using the DFT model B3LYP with the LACVP** pseudopotential basis set as incorporated into the TITAN™ software package.

The relative acidity of anion precursor carbon acids (toluene, 1,3-diboretane and 2-aza-1,3-diboretane) were estimated relative to the acidity of cyclopentadiene by comparing the enthalpies (ΔΔH) of the model reactions:

XC—H+Cp⁻→XC⁻+CpH where

XC—H is the carbon acid precursor,

Cp— is the cyclopentadienyl anion,

XC— is the anionic ligand precursor and

CpH is cyclopentadiene.

Based on these estimates, 1,3-diboretane (ΔΔH=−7.1 kcal/mole) is more acidic than either toluene (ΔΔH=28.0 kcal/mole) or cyclopentadiene (ΔΔH=0 kcal/mole). The calculations also indicate that 2-aza-1,3-diboretane (ΔΔH=25.9 kcal/mole) is more acidic than toluene though less acidic than cyclopentadiene). Thus, the routinely used eprotonating agents (e.g., alkyllithium or alkylpotassium compounds) are asic enough to generate the corresponding 1,3-diboretanyl and 2-aza-1,3-diboretanyl anions.

To estimate the effect of ligands (L and L') on the relative stability of the zirconocenium active sites, we use the relative enthalpy (ΔΔH$_f$) of the reaction:

LL'ZrMe₂→LL'ZrMe⁺+Me⁻ compared with the enthalpy of a standard process in which the zirconium is bonded to two cyclopentadienyl ligands:

Cp₂ZrMe₂→Cp₂ZrMe⁺+Me⁻

According to these estimates (Table 1), the 1,3-diboretanyl ligand should stabilize an electrophilic active site somewhat less effectively compared with a cyclopentadienyl ligand and significantly less compared with an indenyl or fluorenyl ligand. The same calculations, however, predict that the 2-aza-1,3-diboretanyl ligand will stabilize the electrophilic active site more effectively than cyclopentadienyl.

TABLE 1

| Complex | ΔΔH$_f$, kcal/mole |
|---|---|
| Cp₂ZrMe₂ | 0 |
| (Ind)(Cp)ZrMe₂ | −6.9 |
| (Flu)(Cp)ZrMe₂ | −10.4 |
| (1,3-diboretanyl)(Cp)ZrMe₂ | 5 |
| (2-aza-1,3-diboretanyl)(Cp)ZrMe₂ | −5 |

The increased stability of the active site for the 2-aza-1,3-diboretanyl complex permits a high concentration of active sites in the polymerization process, which results in a more active catalyst.

Remarkably, the increased stability of the zirconocenium cation with the 2-aza-1,3-diboretanyl ligand results only in a minor reduction (<2 kcal/mole) in its reactivity toward ethylene as characterized by the calculated heat of interaction upon pi-complexation as compared to the bis (cyclopentadienyl) zirconocenium ion (Table 2).

TABLE 2

| Active site | Relative heat of interaction of active site with ethylene, kcal/mol |
|---|---|
| Cp₂ZrMe+ | 0 |
| (Ind)(Cp)ZrMe+ | 3.6 |
| (Flu)(Cp)ZrMe+ | 4.2 |
| (1,3-diboretanyl)(Cp)ZrMe+ | −0.5 |
| (2-aza-1,3-diboretanyl)(Cp)ZrMe+ | 1.8 |

Further calculations were performed to compare the E$_a$ for ethylene insertion:

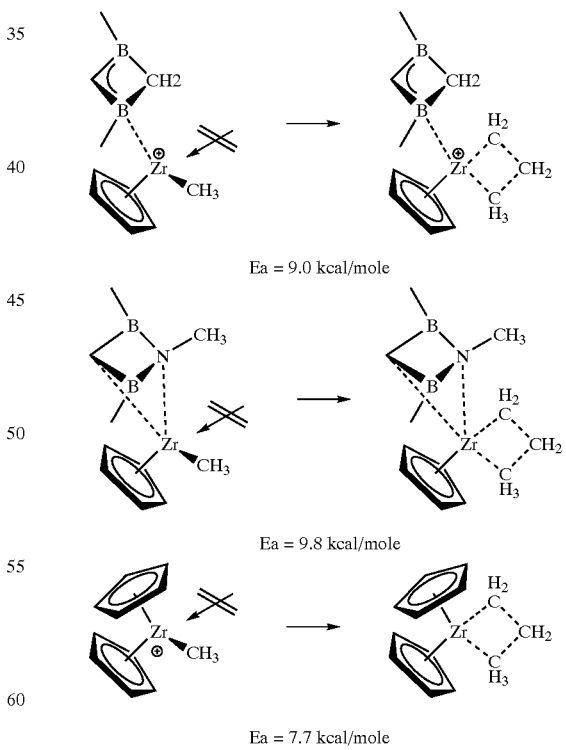

These calculations show a somewhat higher activation energy (i.e., a somewhat less facile reaction) for ethylene insertion in the case of a 1,3-diboretanyl or 2-aza-1,3-diboretanyl complex compared with cyclopentadienyl.

The preceding examples are meant only as illustrations. The following claims define the invention.

I claim:

1. A catalyst system which comprises:
   (a) an activator; and
   (b) an organometallic complex comprising a Group 3 to 10 transition or lanthanide metal, M, and at least one anionic 1,3-diboretanyl ligand that is bonded to M.

2. The catalyst system of claim 1 wherein the activator is selected from the group consisting of alkyl alumoxanes, alkylaluminum compounds, aluminoboronates, organoboranes, ionic borates, and ionic aluminates.

3. The catalyst system of claim 1 wherein the complex includes a Group 4 transition metal.

4. The catalyst system of claim 1 wherein the complex further comprises a substituted or unsubstituted cyclopentadienyl, indenyl, or fluorenyl group.

5. The catalyst system of claim 1 wherein the complex further comprises a polymerization-stable, anionic ligand selected from the group consisting of boraaryl, pyrrolyl, indolyl, quinolinoxy, pyridinoxy, indenoindolyl, and azaborolinyl.

6. The catalyst system of claim 1 wherein the 1,3-diboretanyl ligand is bridged to another ligand.

7. The catalyst system of claim 1 wherein the 1,3-diboretanyl ligand has the structure:

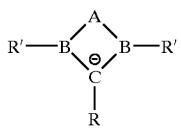

in which A is selected from the group consisting of O, S, NR, PR, and $CR_2$; and each of R and R' is independently selected from the group consisting of hydrogen, $C_1$–$C_{30}$ hydrocarbyl, dialkylamino, halide, and organosilyl.

8. The catalyst system of claim 1 wherein the complex has the structure:

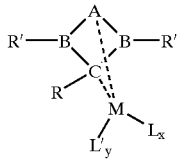

wherein M is a Group 3 to 10 transition or lanthanide metal; A is selected from the group consisting of O, S, NR, PR, and $CR_2$; and each of R and R' is independently selected from the group consisting of hydrogen, $C_1$–$C_{30}$ hydrocarbyl, dialkylamino, halide, and organosilyl; each L is independently selected from the group consisting of halide, alkoxy, siloxy, alkylamino, and $C_1$–$C_{30}$ hydrocarbyl; L' is selected from the group consisting of substituted or unsubstituted cyclopentadienyl, indenyl, fluorenyl, boraaryl, pyrrolyl, indolyl, indenoindolyl, quinolinoxy, pyridinoxy, and azaborolinyl; y is 0 or 1; and x+y satisfies the valence of M.

9. A supported catalyst system of claim 1.

10. A process which comprises polymerizing an olefin in the presence of the catalyst system of claim 1.

11. A process which comprises copolymerizing ethylene with a $C_3$–$C_{10}$ α-olefin in the presence of the catalyst system of claim 1.

12. A method which comprises deprotonating a 1,3-diboretane and reacting the resulting 1,3-diboretanyl anion with a Group 3 to 10 transition or lanthanide metal source to produce an organometallic complex comprising the metal, M, and at least one anionic 1,3-diboretanyl ligand that is bonded to M.

13. A method which comprises reacting a synthetic equivalent of a 1,3-diboretanyl anion with a Group 3 to 10 transition or lanthanide metal source to produce an organometallic complex comprising the metal, M, and at least one 1,3-diboretanyl ligand that is bonded to M.

14. The method of claim 13 wherein the synthetic equivalent has the structure:

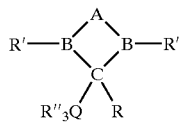

in which A is selected from the group consisting of O, S, NR, PR, and $CR_2$; each of R and R' is independently selected from the group consisting of hydrogen, $C_1$–$C_{30}$ hydrocarbyl, dialkylamino, halide, and organosilyl; Q is Si, Sn, or Ge; and each R" is independently $C_1$–$C_{30}$ hydrocarbyl.

* * * * *